(12) United States Patent
Justin et al.

(10) Patent No.: US 8,349,010 B2
(45) Date of Patent: *Jan. 8, 2013

(54) EXPANDING LIGAMENT GRAFT FIXATION SYSTEM

(75) Inventors: Daniel F. Justin, Logan, UT (US); Richard F. Wenstrom, Jr., Norwood, MA (US); Andrew S. Levy, Summit, NJ (US)

(73) Assignee: DePuy Mitek, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/009,907

(22) Filed: Jan. 20, 2011

(65) Prior Publication Data
US 2011/0112641 A1    May 12, 2011

Related U.S. Application Data

(63) Continuation of application No. 11/299,493, filed on Dec. 9, 2005, now Pat. No. 7,901,456, which is a continuation of application No. 11/098,199, filed on Apr. 4, 2005, now Pat. No. 7,008,451, which is a continuation of application No. 09/966,737, filed on Sep. 28, 2001, now Pat. No. 6,887,271.

(51) Int. Cl.
*A61F 2/08*    (2006.01)
(52) U.S. Cl. .................... 623/13.14; 623/13.13; 606/313
(58) Field of Classification Search .......... 606/300–301, 606/304, 309, 313, 314, 316, 318, 321, 65–68; 623/13.11–13.19
See application file for complete search history.

(56) References Cited

U.S. PATENT DOCUMENTS

| | | |
|---|---|---|
| RE13,204 E | 2/1911 | Jossart |
| 2,353,851 A | 7/1944 | Rosan |
| 3,153,975 A | 10/1964 | Rapata |
| 3,199,398 A | 8/1965 | Weisz |
| 3,411,397 A | 11/1968 | Birmingham |
| 3,516,324 A | 6/1970 | Berner |
| 3,678,798 A | 7/1972 | Van Niel |
| 3,731,724 A | 5/1973 | Dorflinger |
| 3,765,295 A | 10/1973 | Ptak |
| 3,832,931 A | 9/1974 | Talan |

(Continued)

FOREIGN PATENT DOCUMENTS

CA    1015989    8/1977

(Continued)

OTHER PUBLICATIONS

Sklar, "Intrafix.TM. Technique for Tibial Fixation of ACL Grafts" Innovasive Devices, a company brochure of Mitek Products, Ethicon 1999—U.S. Appl. No. 09/304,885, Sklar et al., filed May 4, 1999.

(Continued)

*Primary Examiner* — Paul Prebilic

(57) ABSTRACT

A graft fixation system for fixing graft material in a bone tunnel includes an expandable fixation member having a graft receiving eyelet disposed proximate its distal end, opposed bone engaging elements disposed about its periphery, and an expansion plug receiving opening defined in its proximal end. The system also includes an expansion plug having a diameter greater than the diameter of the expansion plug receiving opening so that forceble insertion of the expansion plug into the expansion plug receiving opening causes an expansion of the expandable fixation member driving the opposed bone engaging elements apart so as to fix the bone engaging elements, as well as the graft material, in a bone tunnel.

18 Claims, 6 Drawing Sheets

U.S. PATENT DOCUMENTS

| | | |
|---|---|---|
| 3,942,407 A | 3/1976 | Mortensen |
| 3,976,079 A | 8/1976 | Samuels et al. |
| 4,083,289 A | 4/1978 | Erickson |
| 4,085,651 A | 4/1978 | Koscik |
| 4,407,618 A | 10/1983 | Kimura |
| 4,484,570 A | 11/1984 | Sutter et al. |
| 4,535,925 A | 8/1985 | Ramey et al. |
| 4,580,936 A | 4/1986 | Francis et al. |
| 4,590,928 A | 5/1986 | Hunt et al. |
| 4,708,132 A | 11/1987 | Silvestrini |
| 4,708,397 A | 11/1987 | Weinmann |
| 4,716,893 A | 1/1988 | Fischer et al. |
| 4,744,793 A | 5/1988 | Parr et al. |
| 4,755,183 A | 7/1988 | Kenna |
| 4,778,468 A | 10/1988 | Hunt et al. |
| 4,784,126 A | 11/1988 | Hourahane |
| 4,828,562 A | 5/1989 | Kenna |
| 4,851,005 A | 7/1989 | Hunt et al. |
| 4,870,957 A | 10/1989 | Goble et al. |
| 4,927,421 A | 5/1990 | Goble et al. |
| 4,940,467 A | 7/1990 | Tronzo |
| 4,944,742 A | 7/1990 | Clemow et al. |
| 4,950,270 A | 8/1990 | Bowman et al. |
| 4,950,271 A | 8/1990 | Lewis et al. |
| 5,013,316 A | 5/1991 | Goble et al. |
| 5,037,422 A | 8/1991 | Hayhurst et al. |
| 5,062,843 A | 11/1991 | Mahony, III |
| 5,108,431 A | 4/1992 | Mansat et al. |
| 5,147,362 A | 9/1992 | Goble |
| 5,151,104 A | 9/1992 | Kenna |
| 5,152,790 A | 10/1992 | Rosenberg et al. |
| 5,211,647 A | 5/1993 | Schmieding |
| 5,234,430 A | 8/1993 | Huebner |
| 5,236,445 A | 8/1993 | Hayhurst et al. |
| 5,268,001 A | 12/1993 | Nicholson et al. |
| 5,282,802 A | 2/1994 | Mahony, III |
| 5,312,438 A | 5/1994 | Johnson |
| 5,314,427 A | 5/1994 | Goble et al. |
| 5,324,308 A | 6/1994 | Pierce |
| 5,356,435 A | 10/1994 | Thein |
| 5,360,448 A | 11/1994 | Thramann |
| 5,360,450 A | 11/1994 | Giannini |
| 5,376,119 A | 12/1994 | Zimmermann |
| 5,383,878 A | 1/1995 | Roger et al. |
| 5,425,707 A | 6/1995 | Goldberg |
| 5,425,767 A | 6/1995 | Steininger |
| 5,454,811 A | 10/1995 | Huebner |
| 5,458,601 A | 10/1995 | Young et al. |
| 5,464,427 A | 11/1995 | Curtis et al. |
| 5,470,334 A | 11/1995 | Ross et al. |
| 5,480,403 A | 1/1996 | Lee et al. |
| 5,486,197 A | 1/1996 | Le et al. |
| 5,489,210 A | 2/1996 | Hanosh |
| 5,562,669 A | 10/1996 | McGuire |
| 5,584,835 A | 12/1996 | Greenfield |
| 5,618,314 A | 4/1997 | Jamiolkowski et al. |
| 5,632,748 A | 5/1997 | Beck, Jr. et al. |
| 5,645,589 A | 7/1997 | Li |
| 5,702,397 A | 12/1997 | Goble et al. |
| 5,707,395 A | 1/1998 | Li |
| 5,725,529 A | 3/1998 | Nicholson et al. |
| 5,776,196 A | 7/1998 | Matsuzaki et al. |
| 5,895,425 A | 4/1999 | Grafton et al. |
| 5,899,938 A | 5/1999 | Sklar et al. |
| 5,906,632 A | 5/1999 | Bolton |
| 5,918,604 A | 7/1999 | Whelan |
| 5,948,001 A | 9/1999 | Larsen |
| 5,961,520 A | 10/1999 | Beck et al. |
| 5,989,253 A | 11/1999 | Bigliardi |
| 6,099,530 A | 8/2000 | Simonian et al. |
| 6,132,433 A | 10/2000 | Whelan |
| 6,283,973 B1 | 9/2001 | Hubbard et al. |
| 6,355,066 B1 | 3/2002 | Kim |
| 6,371,124 B1 | 4/2002 | Whelan |
| 6,379,361 B1 | 4/2002 | Beck et al. |
| 6,387,129 B2 | 5/2002 | Rieser et al. |
| 6,517,579 B1 | 2/2003 | Paulos et al. |
| 6,533,816 B2 | 3/2003 | Sklar |
| 6,537,319 B2 | 3/2003 | Whelan |
| 6,554,862 B2 | 4/2003 | Hays et al. |
| 6,562,071 B2 | 5/2003 | Jarvinen |
| 6,575,987 B2 | 6/2003 | Gellman et al. |
| 6,616,694 B1 | 9/2003 | Hart |
| 6,623,524 B2 | 9/2003 | Schmieding |
| 6,632,245 B2 | 10/2003 | Kim |
| 6,673,094 B1 | 1/2004 | McDevitt et al. |
| 6,733,529 B2 | 5/2004 | Whelan |
| 6,746,483 B1 | 6/2004 | Bojarski et al. |
| 6,887,271 B2 | 5/2005 | Justin et al. |
| 6,932,841 B2 | 8/2005 | Sklar et al. |
| 6,939,379 B2 | 9/2005 | Sklar |
| 7,008,451 B2 | 3/2006 | Justin et al. |
| 7,083,647 B1 | 8/2006 | Sklar et al. |
| 7,261,716 B2 | 8/2007 | Strobel et al. |
| 7,309,355 B2 | 12/2007 | Donnelly et al. |
| 7,329,281 B2 | 2/2008 | Hays |
| 7,578,844 B2 | 8/2009 | Sklar et al. |
| 7,637,949 B2 | 12/2009 | Hart |
| 7,901,456 B2 * | 3/2011 | Justin et al. ............... 623/13.14 |
| 2001/0007074 A1 | 7/2001 | Strobel et al. |
| 2001/0047206 A1 | 11/2001 | Sklar et al. |
| 2002/0007182 A1 | 1/2002 | Kim |
| 2002/0040241 A1 | 4/2002 | Jarvinen |
| 2002/0072797 A1 | 6/2002 | Hays et al. |
| 2003/0065390 A1 | 4/2003 | Justin et al. |
| 2003/0135274 A1 | 7/2003 | Hays et al. |
| 2003/0144735 A1 | 7/2003 | Sklar et al. |
| 2003/0191530 A1 | 10/2003 | Sklar |
| 2004/0059415 A1 | 3/2004 | Schmieding |
| 2004/0068262 A1 | 4/2004 | Lemos et al. |
| 2004/0194789 A1 | 10/2004 | Whelan |
| 2004/0267361 A1 | 12/2004 | Donnelly et al. |
| 2005/0159748 A1 | 7/2005 | Clark |
| 2005/0171603 A1 | 8/2005 | Justin et al. |
| 2005/0216012 A1 | 9/2005 | Willimen |
| 2006/0052787 A1 | 3/2006 | Re et al. |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0149258 A1 | 7/2006 | Sousa |
| 2006/0189991 A1 | 8/2006 | Bickley |
| 2007/0005069 A1 | 1/2007 | Contiliano et al. |
| 2008/0015710 A1 | 1/2008 | Hays et al. |
| 2008/0133007 A1 | 6/2008 | Donnelly et al. |
| 2008/0154314 A1 | 6/2008 | McDevitt |
| 2008/0161806 A1 | 7/2008 | Donnelly et al. |
| 2008/0161864 A1 | 7/2008 | Beck et al. |
| 2008/0228271 A1 | 9/2008 | Stone et al. |
| 2010/0121449 A1 | 5/2010 | Sklar et al. |
| 2011/0112641 A1 | 5/2011 | Justin et al. |

FOREIGN PATENT DOCUMENTS

| | | |
|---|---|---|
| DE | 4127550 | 2/1993 |
| EP | 0358372 | 3/1990 |
| EP | 0425140 | 5/1991 |
| EP | 596177 | 5/1994 |
| EP | 0596829 | 5/1994 |
| EP | 611557 | 8/1994 |
| EP | 0651979 | 5/1995 |
| EP | 0834281 | 4/1998 |
| EP | 1491162 | 12/2004 |
| FR | 2590792 | 6/1987 |
| FR | 2636835 | 3/1990 |
| FR | 2725615 | 4/1996 |
| JP | 5-300917 | 11/1993 |
| JP | 8066410 | 3/1996 |
| WO | WO 9428799 | 12/1994 |
| WO | WO 9822047 | 5/1998 |
| WO | WO 9823229 | 6/1998 |
| WO | WO 9952472 | 10/1999 |
| WO | WO 01/06909 | 2/2001 |
| WO | WO 0130253 | 5/2001 |
| WO | WO 01/95835 | 12/2001 |
| WO | WO 02/32345 | 4/2002 |

OTHER PUBLICATIONS

European Search Report, from 11156055.3, dated Apr. 15, 2011.

* cited by examiner

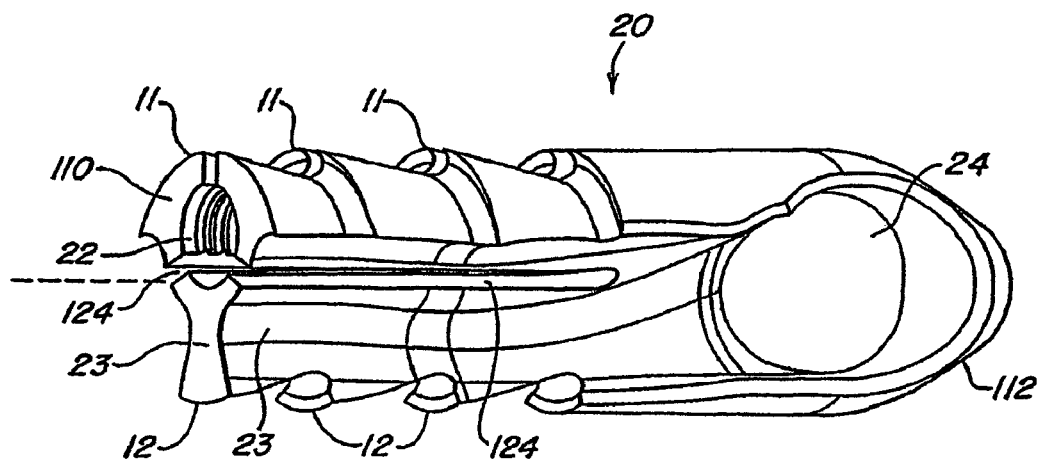
FIG. 2
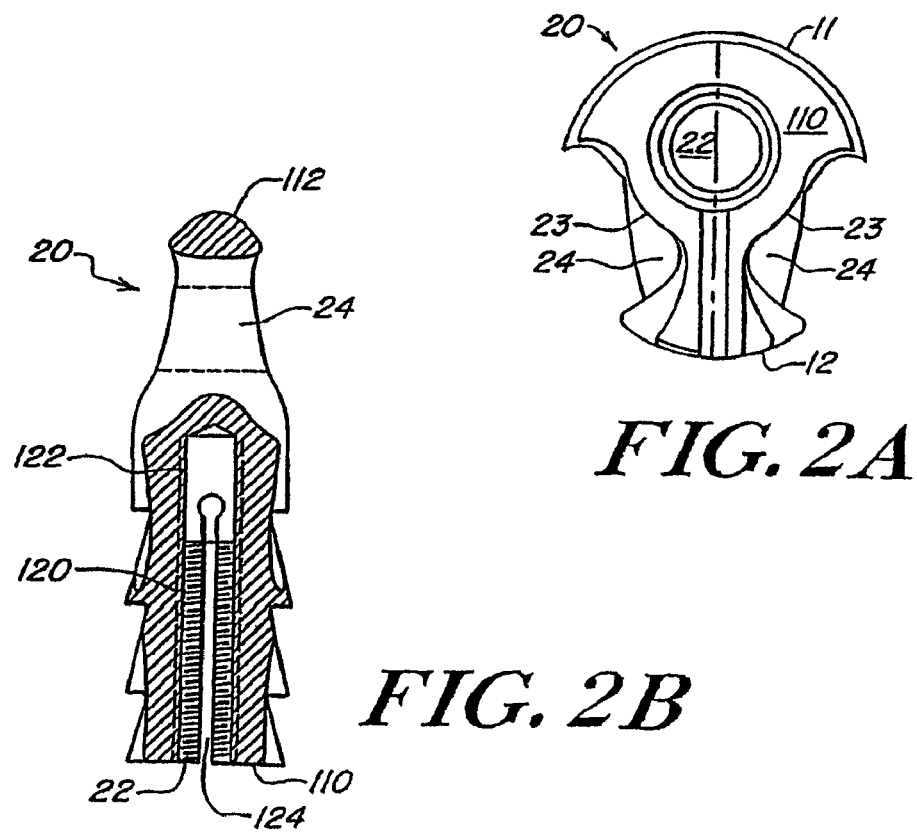
FIG. 2A
FIG. 2B

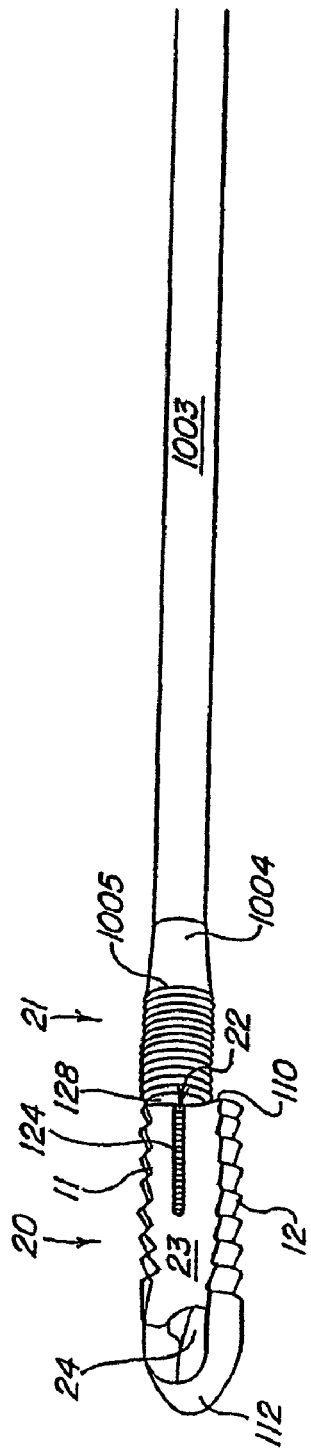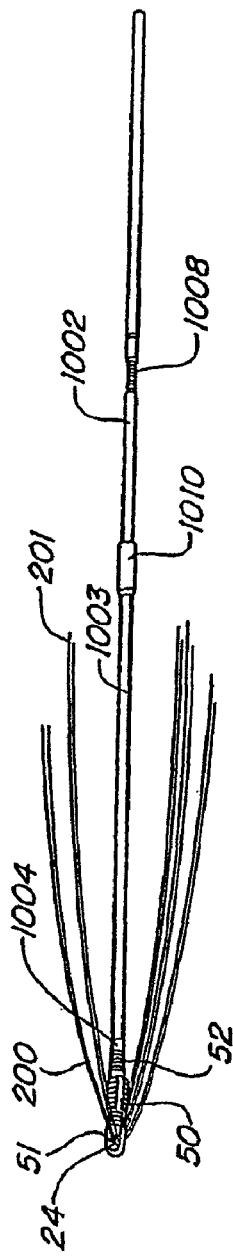

EXPANDING LIGAMENT GRAFT FIXATION SYSTEM

RELATED APPLICATIONS

This application is a continuation of U.S. patent application Ser. No. 11/299,493, filed on Dec. 9, 2005, now U.S. Pat. No. 7,901,456, issued Mar. 8, 2011, which is a continuation of U.S. patent application Ser. No. 11/098,199, filed on Apr. 4, 2005, now U.S. Pat. No. 7,008,451, issued Mar. 7, 2006, which is a continuation of U.S. patent application Ser. No. 09/966,737, filed on Sep. 28, 2001, now U.S. Pat. No. 6,887,271, issued May 3, 2005.

FIELD OF THE INVENTION

The present invention relates to systems and methods for locking and integrating soft tissue with bone. More specifically, systems and methods for use in conjunction with ligament replacement surgery are described.

BACKGROUND OF THE INVENTION

The complete or partial detachment of ligaments, tendons or other soft tissues (hereinafter "ligamentary material") from the bones with which they are associated are commonplace, particularly among athletes. Such injuries usually result from excessive stress being applied on these tissues. Some degree of tissue detachment may occur, for instance, as the result of an accident, overexertion during a work-related activity, stress during the course of an athletic event, or in conjunction with numerous other situations and activities. If, however, ligamentary material is completely detached from its associated bone(s) or is severed, partial or permanent disability may result.

Fortunately, there are numerous surgical techniques known and used in the art for reattaching detached tissues and/or completely replacing ligamentary material. One such technique involves the use of "traditional" fasteners (e.g. metal staples, cancellous bone screws.) Such fasteners have also been used to attach tendon or ligament substitutes (often formed of autogenous tissue harvested from elsewhere in the body, collectively referred to herein as "grafts" or "graft material") to the desired bone(s). A common surgery involves replacing or repairing the anterior cruciate ligament (ACL) in a human knee. Bone tunnels are appropriately aligned and formed in both the proximal tibia and the distal femur during the course of this surgery. Graft material is somehow rigidly coupled, usually with bone blocks to be inserted into these tunnels, to fix the material in a proper position for long term use in the body.

Such ligament fixation schemes have not been entirely successful. For example, rigid attachment using "traditional" attachment devices such as staples, sutures and screws often cannot be maintained even under normal tensile loads. Also, the use of sharp screws to create a locking interference fit between a bone plug/block and a bone tunnel may be problematic. For instance, there is always the possibility of damaging the ligament during insertion of the screw. In addition, it may be difficult to maintain the desired tension on the graft material during insertion of the screw. Alternative, non-rigid fixation schemes (such as suspending a ligament graft from a suture button) also have drawbacks. Because the graft structure is not, in such schemes, rigidly fixed within the bone tunnels, movement of the graft structure may disrupt the healing process. It is known that intimate contact between the graft material and the walls of the bone tunnels aids in ensuring an effective, efficient healing process.

Another potential problem may arise even where the graft material appears to be successfully fixed within the bone tunnel. Bone tunnels are usually drilled for a considerable length into the femur for fixation of the graft material in ACL replacement procedures. Where exactly within the tunnel the graft is fixed often depends on the manner of fixation and tensioning of the graft material, but often the site for fixation is chosen as the place where the fixation device best allows fixing. Where the fixation takes place inside the bone tunnel apart from the bone tunnel edge at the distal end of the femur, the graft material that extends from the fixation point to the edge of the bone tunnel often moves or slides within this remaining portion of the tunnel. This phenomenon is known to some surgeons as the "windshield wiper" effect. As noted above, movement tends to prevent healing and fixation of the soft tissue to bone, so where the windshield wiper effect occurs, the portion of the graft that moves when the patient uses the reconstructed joint may never heal completely in the region near the edge of the bone tunnel. This potential problem defeats the goal of most surgeons which is to have the graft material fix as close as possible to its natural fixation point before being damaged by injury or disease. This natural fixation point is generally at the edge of the bone tunnel, where the graft will not fix if the windshield wiper effect is present.

Accordingly, there is a need for ligament graft fixation devices that reliably provide fixation of graft material in the region closest to the natural fixation point of the ligamentary material being replaced.

SUMMARY OF THE INVENTION

The present invention provides a ligament graft fixation system for fixing ligament graft material within a bone tunnel in a way that better approximates the natural fixation point of the ligamentary material that is being replaced. The system of the invention includes an expandable fixation member having a graft receiving eyelet disposed proximate its distal end, opposed bone engaging elements disposed about its periphery, and an expansion plug receiving opening defined in its proximal end. The system also includes an expansion plug having a diameter greater than the diameter of the expansion plug receiving opening so that forcible insertion of the expansion plug into the expansion plug receiving opening causes an expansion of the expandable fixation member to drive the opposed bone engaging elements apart so as to fix the bone engaging elements, as well as the graft material, in a bone tunnel. The fixation system of the invention allows for fixation at the proximal end of the fixation member, which can be placed proximate to the edge of the bone tunnel to fix the graft as close to the anatomically correct position as desired.

Specific embodiments of the fixation system of the invention include those having graft receiving grooves extending distally from the eyelet, including embodiments where the grooves are asymmetrically placed to allow anterior or posterior fixation at the surgeon's discretion. Expansion slots can also be provided to specifically direct the expansion of the fixation member so that the expansion can not only engage the bone engaging elements with the wall of the bone tunnel, but also urge the graft material into closer association with the bone tunnel wall.

In still other embodiments, the graft receiving eyelet can be provided on a separate tip that includes a proximal expansion plug that can forcibly mate with a distal plug receiving opening on the fixation member. In this embodiment, proximal and distal expansion slots can be provided, and in some cases, the proximal and distal expansion slots can encourage expansion in different directions. For example, one or more distal slots can be employed to encourage expansion in a direction that will drive the opposed bone engaging elements apart so as to fix the fixation member to bone, while the one or more proximal slots can encourage expansion in a direction that will urge the graft material into closer contact with the bone tunnel walls. In this embodiment, it may be desirable to size the plugs and plug receiving openings to allow the proximal plug to enter the distal plug receiving opening first upon compressing the system to forcibly engage the plugs so that the graft material does not bunch up upon fixation. This specific embodiment provides still more proximal fixation which can be provided near the edge of a bone tunnel as desired.

Insertion and activation elements can also be provided. In any of the previously mentioned embodiments, a pull rod can extend through the expansion plug and engage the distal-most element of the system while a cannulated push tube can slide over the pull rod to engage the expansion plug. Relative movement between the pull rod and the push tube can then forcibly engage the elements.

In a method of the invention, a bone tunnel can first be formed, then a fixation system as described above can be loaded with graft material through the eyelet, and the fixation system and graft material can be inserted into the bone tunnel. Insertion into the bone tunnel can stop when the proximal end of the fixation member is substantially even with or slightly inside the edge of the bone tunnel. The fixation system can then be actuated to fix the fixation member and the graft proximate to the edge of the bone tunnel in the desired anatomically correct position.

BRIEF DESCRIPTION OF THE DRAWINGS

The invention will be more fully understood from the following detailed description taken in conjunction with the accompanying drawings.

FIGS. 2, 2A and 2B are perspective, end and cross-sectional views of an expanding fixation member of the graft fixation system of FIG. 1;

FIG. 4 is a side view of the graft fixation system of FIG. 1 without graft material;

FIG. 5 is a side view of a graft fixation system of the invention having a separate distal tip;

DETAILED DESCRIPTION OF THE INVENTION

Figure 1:
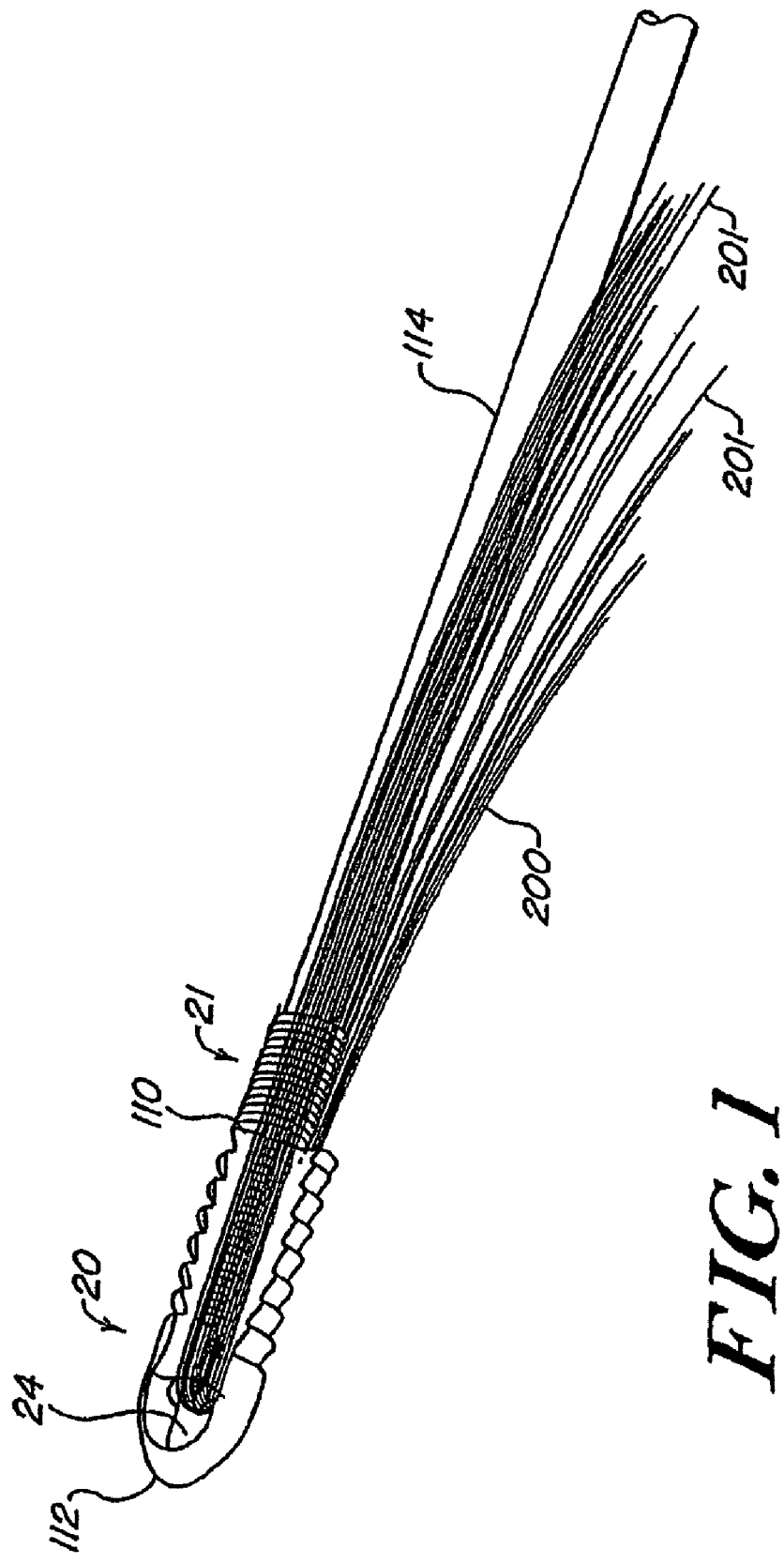
FIG. 1 is a side view of a graft fixation system of the invention loaded with graft material and mounted on an insertion member.

The present invention provides a device, system, and method useful for fixing soft tissue graft material within a bone tunnel to replace damaged ligamentary material and restore function to the portion of a patient's body in which the damaged ligamentary material was located. FIG. 1 provides an illustration of one such system of the invention having a fixation member 20, an expansion plug 21 positioned at a proximal end 110 of the fixation member, and a graft material holding element in the form of an eyelet 24 located proximate to a distal end 112 of the fixation member. Graft material 200 can be passed through eyelet 24 so that two ends 201 of the graft trail fixation member 20 proximally. An insertion element 114 mates with fixation member 20 and expansion plug 21 and extends proximally. In use, a surgeon inserts fixation member 20 along with graft material 200 into a prepared bone tunnel using insertion element 114 until the graft and fixation member are in the desired position for graft fixation within the tunnel. Insertion element 114 can then be actuated or manipulated by the surgeon to force expansion plug 21 distally into fixation member 20 to cause the fixation member to expand and thereby fix the graft material to the interior of the bone tunnel. Further details of this and other embodiments of the invention are provided by reference to further FIGS. below.

As can be seen in FIGS. 2, 2A and 2B (which illustrate a side view, a proximal end view, and a lengthwise cross-section, respectively, of fixation member 20), fixation member 20 includes cut out passages or grooves 23 extending proximally along the fixation member from each of the two opposed sides of eyelet 24. In general, fixation member 20 will be sized to fit closely into a bone tunnel of predetermined size. Typical grafts used to replace ligamentary material are compressible, and grooves 23 will be sized so that the graft material will be snugly pressed between the walls of the bone tunnel and grooves 23 upon insertion of the fixation system into the tunnel.

Fixation member 20 also includes a proximal expansion plug receiving opening 22 which extends distally within the body of the fixation member. Opening 22 is threaded in the illustrated embodiment in two regions. A first threaded region 120, close to proximal end 110 of fixation member 20, is threaded so as to engage expansion plug 21 when the plug is forced into the fixation member and lock the plug in place. A second threaded region 122, distal to region 120, is threaded to engage a pull rod 1002 (further described with respect to FIG. 3 below) that may be provided as part of insertion element 114.

On its external surfaces, fixation member 20 has a rounded or bullet shaped distal end to aid the surgeon in directing the fixation member into a bone tunnel. In addition, about its outer circumference (and generally not within grooves 23), fixation member 20 includes a series of opposed bone engaging elements 11, 12. As illustrated, bone engaging elements 11, 12 are fins that are angled proximally so that while they can slide into a bone tunnel relatively easily, it will be more difficult to pull fixation member 20 from a bone tunnel after insertion as the fins will dig into the walls of the bone tunnel (especially after expansion of the fixation element). While bone engaging elements 11, 12 in this illustrated embodiment are angled fins, a person of ordinary skill in the art will recognize that other bone engaging elements known in the art, including for example asymmetric wedges, nitinol arcs, or mechanical elements that spring into cancellous bone, may be used as bone engaging elements on fixation member 20 within the spirit of the invention.

One or more expansion slots 124 are also provided (two such slots 124 are illustrated in FIG. 2) on fixation member 20 beginning at the proximal end 110 of the fixation member and extending distally through threaded region 120, generally extending at least as far as expansion plug 21 will be inserted into the fixation member. Slots 124 preferably do not extend through the entirety of threaded region 122 to which a pull tool may be attached as such an extension of slots 124 might weaken the engagement between the pull tool and the fixation member. A person of ordinary skill in the art will recognize that the number and position of the one or more expansion slots 124 can be varied from the number (two) and positions illustrated in FIG. 2 within the spirit of the invention to allow fixation member 20 to expand upon insertion of expansion plug 21 so as to fix graft material to a bone tunnel wall. In particular, slot or slots 124 should be placed so as to result in an expansion of fixation member 20 so that bone engaging elements 11 and 12 move in opposed directions to force the bone engaging elements into engagement contact with the bone tunnel wall to lock the fixation member in place within the bone tunnel. It may also be desirable to place the slot or slots 120 so that fixation member 20 expands so as to force graft material pressed between grooves 23 and the bone tunnel wall into even more intimate contact therewith.

As can be seen in FIGS. 2 and 2A, bone engaging elements 11, 12 have different lengths about the circumference of fixation member 20, with bone engaging elements 11 being larger and having a greater fixation region than bone engaging elements 12. This difference in size results from an asymmetric placement of grooves 23. Each of the two grooves 23 are specifically displaced in a direction toward bone engaging elements 12 as the grooves extend generally proximally from graft eyelet 24. This asymmetry allows a surgeon to select a preferred direction for fixation of graft material within a bone tunnel. For example, for an ACL replacement surgery requiring graft fixation in a bone tunnel formed in a patient's distal femur, the surgeon, for reasons of preference or owing to a specific fixation scheme, may wish to have a more anterior or more posterior fixation of the graft material. Because graft material will be captured between grooves 23 and the walls of the bone tunnel, and because in the illustrated embodiment the grooves are asymmetrically placed, the surgeon may choose to insert the graft/fixation member system so that more of the graft material is captured against the bone tunnel in an anterior or posterior direction.

In addition to asymmetric sizing of bone engaging elements 11, 12, asymmetric placement of grooves 23 can result in asymmetric placement of proximal opening 22. Proximal opening 22 must be placed so that sufficient fixation member 20 material exists to provide strength for threads in threaded region 120 and particularly in threaded region 122 which may be used to securely attach fixation member 20 to a pull tool. Where grooves 23 are displaced toward bone engaging elements 12, this requirement can best be met by placing proximal opening 22 closer to bone engaging elements 11.

Figure 3:
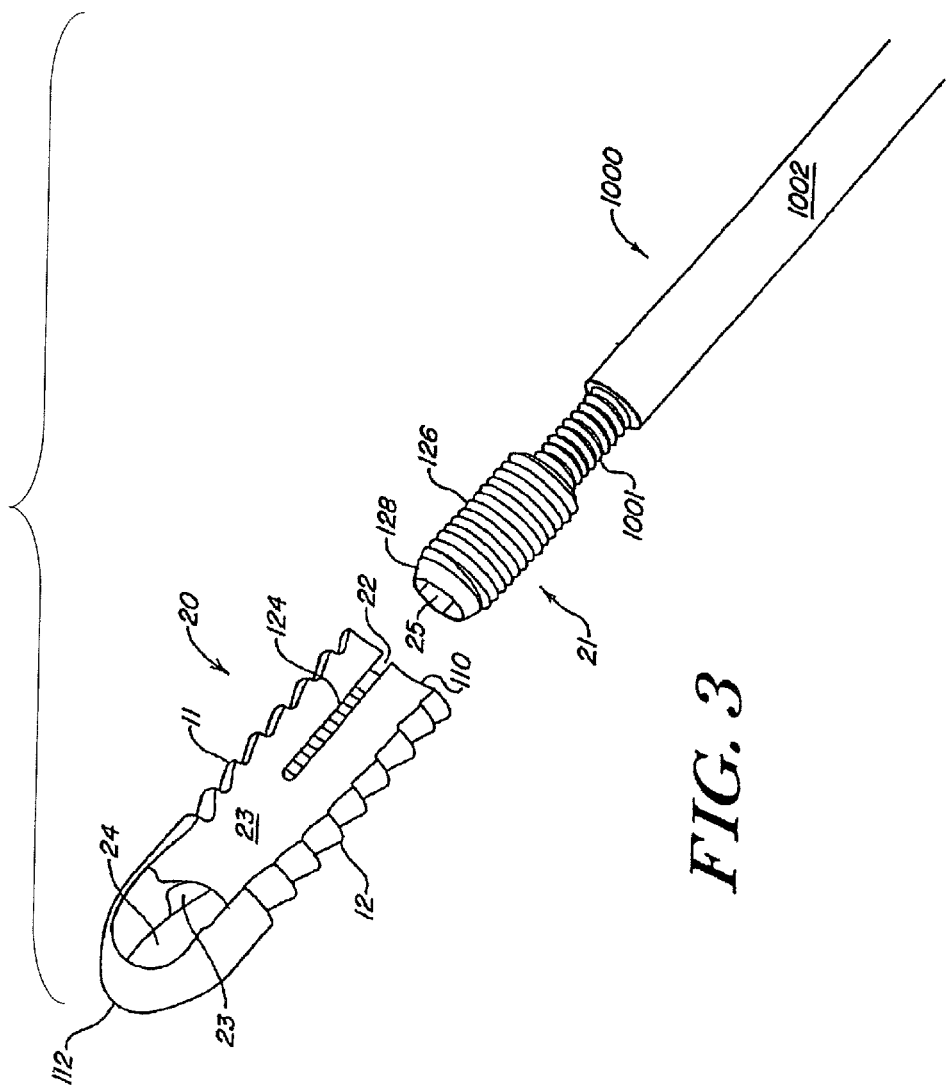
FIG. 3 is an exploded view of the graft fixation system of FIG. 1 including an expanding fixation member, an expansion plug and a pull rod.

Turning now to FIG. 3 (showing an exploded view) and FIG. 4 (showing an assembled fixation assembly of the invention ready for graft placement and fixation), assembly and activation of a system of the invention will be described. FIG. 3 illustrates a fixation member 20, an expansion plug 21, and a pull rod 1002 in exploded view and ready for assembly. As shown in FIG. 3, expansion plug 21 is larger in diameter than proximal plug receiving opening 22 of expansion member 20 so that, upon forcible insertion of expansion plug 21 into opening 22, a forced expansion of fixation member 20 is achieved as described above.

Expansion plug 21 includes external threads 126 which, although larger in diameter than threads in threaded region 120 of opening 22, are preferably of the same pitch as the threads in threaded region 120 so that when the expansion plug has been forced into the opening, threads 126 will engage threaded region 120 to lock expansion plug in place within opening 22. While providing threads 126 and threaded region 120 as elements for locking expansion plug 21 into opening 22 may be convenient for reasons of manufacture, a person of ordinary skill in the art will recognize that a number of other locking elements could be provided such as, for example, expanding locking elements provided on one of the plug or the opening that engage complimentary recesses provided on the other of the plug or the opening, or a pin could be provided on one of the plug or the opening to fit into an L-shaped recess on the other of the plug or the opening so that following insertion and expansion, twisting of one component relative to the other would create a locking relationship that would prevent the plug from backing out of the opening.

Expansion plug 21 may also include a tapered distal 128 configured to ease entry of the expansion plug into opening 22. In addition, the distal end of expansion plug 21 can include a removal tool engaging element such as female hex 25. In the event that threaded expansion plug 21 (which is cannulated as described below) should need to be removed from fixation member 20, a removal tool having a male hex head could be inserted through the plug cannula to engage female hex 25 to "unthread" a plug that would otherwise be locked into place.

In one exemplary embodiment intended for use in fixing graft material in a bone tunnel in a patient's distal femur for replacing a damaged ACL, fixation member 20 can have an overall length of approximately 0.995 inches (with bone engaging elements 11, 12 extending along a length of about 0.390 inches) and a diameter from bone engaging elements 11 to bone engaging elements 12 of about 0.310 inches. Expansion plug 21 can have a major diameter of approximately 0.180 inches and a minor diameter of about 0.160 inches while opening 22 can have a minor diameter of about 0.102 inches and a major diameter of about 0.113 inches. In this same exemplary embodiment, expansion plug 21 can have a length of approximately 0.375 inches while expansion slots 124 can have a length of approximately 0.450 inches. A person of ordinary skill in the art will recognize that these dimensions are provided only to give guidance as to the construction of one embodiment of the invention, and that parts described herein could have other dimensions, especially if tailored to different end uses. The component elements of the invention can be made from a variety of polymers and bio-absorbable polymers known to be useful for implantable medical devices. In one embodiment, each component is formed from Delrin.

Also illustrated in FIG. 3 is pull rod 1002 which is part of insertion element 114 (FIG. 1). Pull rod 1002 is sized pass through cannulated expansion plug 21 and into opening 22 in fixation element 20 where distal threads 1001 are configured to threadedly engage at least threaded portion 122 (FIG. 2B) within opening 22 so as to be releasably engaged to fixation member 20. As further shown in FIG. 4, assembly of the fixation system to insertion element 114 involves sliding expansion plug 21 distally along pull rod 1002 until distal taper region 128 on the plug engages opening 22 on fixation element 20, and sliding push tube 1003 over pull rod 1002 so that a distal end 1005 of the push tube abuts a proximal end of expansion plug 21. In order to provide better surface contact between push tube 1003 and expansion plug 21, a tapered or flared element 1004 may be provided adjacent the distal end of the push tube. So assembled, the fixation system of the invention may be actuated by providing relative movement between pull rod 1002 and push tube 1003 to force expansion plug 21 into opening 22 in fixation element 20 to thereby lock the fixation element into a bone tunnel and fix graft material to the tunnel wall.

In use in ACL replacement surgery, a surgeon would loop graft material 200 through eyelet 24 to result in the configuration illustrated in FIG. 1. The surgeon would next insert fixation element 20 (with attached graft material 200) into a prepared bone tunnel in the distal end of a patient's femur. Fixation element 20 is preferably inserted into the bone tunnel to such a depth that proximal end face 110 of the fixation element is substantially even with or slightly inside the edge of the bone tunnel. The system can then be actuated by holding pull rod 1002 to prevent distal movement of fixation element while pushing on push tube 1003 to force expansion plug 21 into opening 22 of fixation element 20, thereby expanding fixation element to fix the graft within the tunnel. By fixing the graft material in this way, with the fixation element fixing the graft material right to its proximal end 110 and placing the proximal end near the edge of the bone tunnel, the graft will be fixed at or near the edge of the bone tunnel and the "windshield wiper" effect will be reduced or eliminated.

Figure 6:
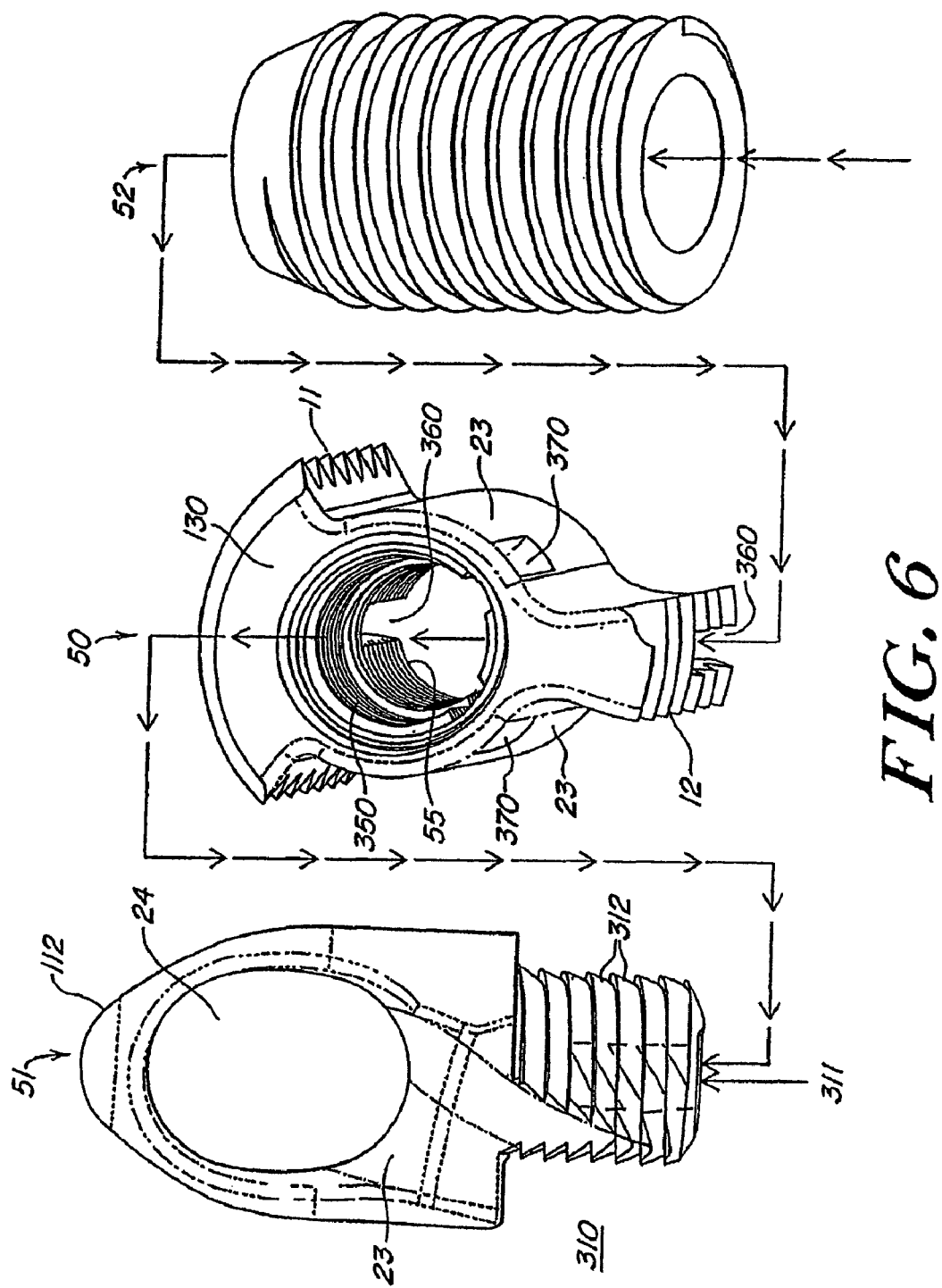
FIG. 6 is a plan view of graft fixation system of FIG. 5.

A further embodiment of the fixation system of the invention is illustrated in FIGS. 5 and 6. In this embodiment, a distal tip 54 having graft receiving eyelet 24 is not integral with fixation member 50. Rather, tip 51 includes a curved or bullet shaped distal end 112, eyelet 24 near the distal end, and a proximal plug 310 that engages fixation member 50. Like expansion plug 21, proximal plug 310 on tip 51 includes threads that are larger in diameter than a distal threaded opening 350 on fixation member 50, but which have the same thread pitch as the threaded opening 350 so that, upon forcible insertion, proximal plug 310 will cause fixation member 50 to expand near its distal end 130 and the threads will lock the tip to the fixation member. Proximal plug 310 can also include an internal threaded region 311 to allow the tip to be fixed to pull rod 1002 so that fixation element 50 may be actuated in the same manner as fixation member 20.

Like fixation member 20 of the previously described embodiment, fixation member 50 has opposed bone engaging elements 11, 12 and asymmetrically placed graft placement grooves 23. Tip 51 can also define a portion of grooves 23 distally from fixation member 50 to eyelet 24. Fixation member 50 also includes a proximal threaded opening 55 for receiving expansion plug 52 in substantially the same way that fixation member 20 receives expansion plug 21.

Fixation member 50 further includes two separate pairs of expansion slots with slots 360 provided proximally to allow expansion from insertion of expansion plug 52 and expansion slots 370 provided distally to allow expansion from insertion of proximal plug 310 of tip 51. As is apparent in the embodiment illustrated in FIG. 6, expansion slots 360, 370 are provided in different orientations to provide differing expansion of fixation member 50 from the insertion of the differing plugs 52, 311, respectively. Distal expansion slots 370 are oriented to allow maximum expansion in a direction to allow bone engaging elements 11, 12 to expand to lock fixation member 50 to a bone tunnel. Proximal expansion slots 360 are oriented to allow maximum expansion in the general direction of grooves 23 so as to force graft material located in the grooves into tighter engagement with the bone tunnel wall near the proximal portion of the fixation element where fixation is most desired.

As is further clear from the embodiment illustrated in FIG. 6, distal threaded opening 350 can have a larger diameter that proximal threaded opening 55. Where proximal plug 310 on tip 51 and expansion plug 52 have approximately the same diameter, this will cause proximal expansion plug 310 to enter distal threaded opening 350 before expansion plug 52 enters proximal threaded opening 55. This can be advantageous where, as here, the distal portion of fixation member 50 expands primarily to lock bone engaging elements 11, 12 into the bone tunnel wall. In this way, fixation member 50 can lock within the tunnel, proximal ends 201 of graft material 200 can be pulled taught by the surgeon, and actuation can continue with expansion plug 52 expanding a proximal portion of fixation member 50 to press the graft material against the bone tunnel wall for optimal fixation. The system of FIGS. 5 and 6 can be inserted and actuated in the same manner as the embodiment of FIGS. 1 to 4.

Figure 7:
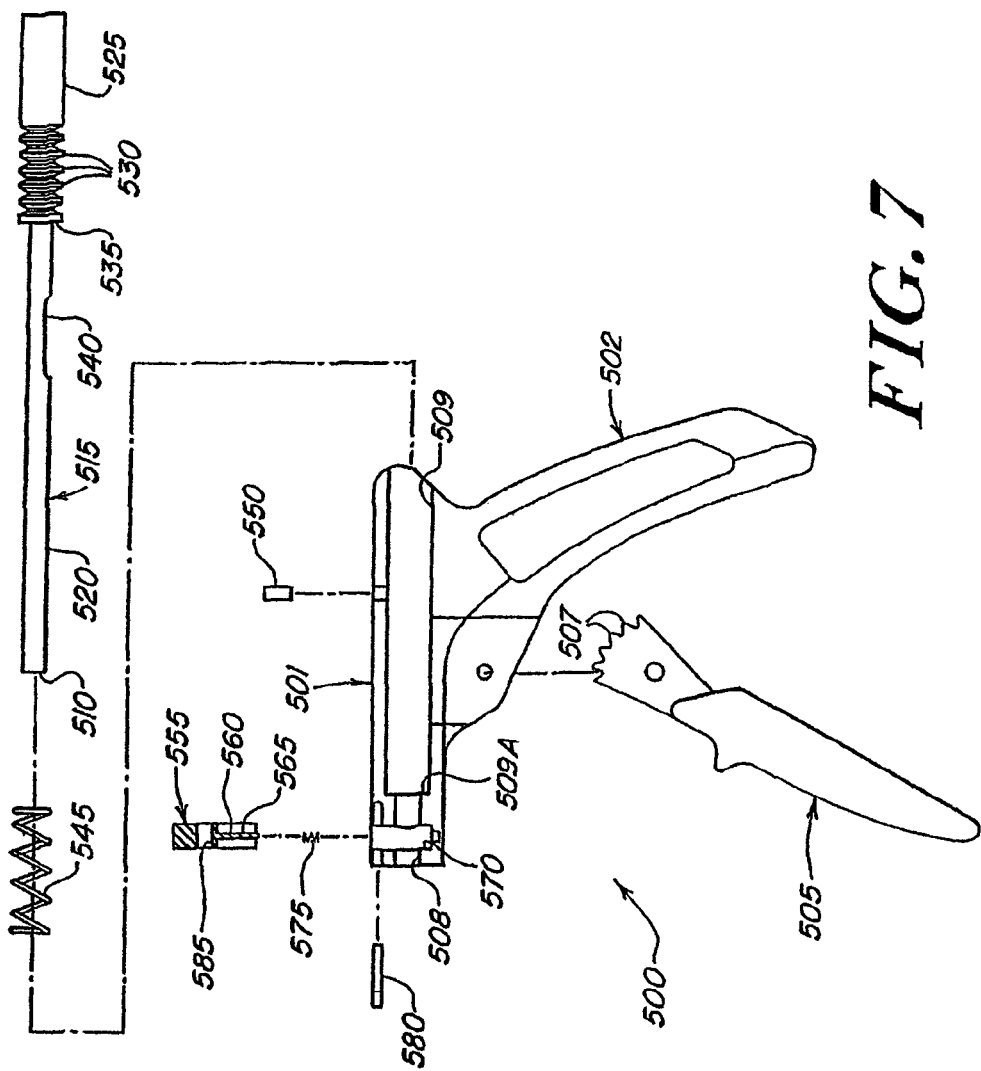
FIG. 7 is a schematic view of an actuation device suitable for use with embodiments of the present invention.

FIG. 7 illustrates a schematic of a delivery device or handle assembly 500 suitable for coupling to pull rod 1002 and push tube 1003 to actuate the illustrated embodiments of the present invention. Handle assembly 500 comprises a body having a handle grip 502. A trigger 505, having a plurality of fingers 507, is pivotally connected to body 501. Body 501 also comprises a bore 508 opening on the body's distal end, and a counterbore 509 opening on the body's proximal end. A shoulder 509A is formed at the intersection of bore 508 and counterbore 509.

Handle assembly 500 also comprises a hollow ram 515. Ram 515 is sized so that it can slidably accommodate pull rod 1002 within its inner diameter and so that it can be coupled to a proximal end of push tube 1003. Ram 515 comprises a narrower distal portion 520 terminating in a distal tip 510, and a wider proximal portion 525 including a plurality of teeth 530. A shoulder 535 is formed at the intersection of narrower distal portion 520 and wider proximal potion 525. A slot 540 extends through the side wall of narrower distal portion 520.

Ram 515 is mounted in body 510 so that (1) the ram's narrower distal portion 520 extends through, and protrudes from, the body's bore 508, (2) the ram's wider proximal portion 525 is disposed in the body's counterbore 509, and (3) the trigger's fingers 507 engage the ram's teeth 530. As a result of this construction, moving trigger 505 will cause ram 515 to move relative to body 501. A spring 545 is positioned in body 501, between body shoulder 509A and ram shoulder 535, so as to bias ram 515 in a proximal direction. A stop pin 550 extends into counterbore 509 So as to limit proximal movement of ram 515.

Handle assembly 500 also comprises a gate 555 which includes an opening 560 therein. Opening 560 defines a bottom wall 565 thereof. Gate 555 is disposed in an opening 570 formed in body 501. A spring 575 biases gate 555 against a locking pin 580, which extends through an oversized hole 585 formed in gate 555. Gate 555 is disposed in body 501 so that the gate's bottom wall 565 normally protrudes, via ram slot 540, into the interior of ram 515; however, pressing gate 555 downward against the power of spring 575 will permit the gate's bottom wall 565 to be removed from the interior of ram 515.

In use handle assembly 500 is loaded over a proximal end of shaft pull rod 1002, and moved proximally down the shaft until the gate's bottom wall 565 starts to engage the ribs 1008 (see FIG. 5) of pull rod 1002. As this occurs, inclined proximal surfaces of ribs 1008 will allow the handle assembly 500 to be moved distally along pull rod 1002 to the extent desired. However, by providing inclined surfaces on only the proximal sides of ribs 1008, the geometry of the ribs can prevent handle assembly 500 from moving back proximally along the shaft, unless, gate 555 is pressed downward against the power of spring 575 so as to move the gate's bottom wall 565 out of engagement with ribs 1008. Handle assembly 500 is moved down pull rod 1002 until the ram's distal end surface 510 engages, or substantially engages, the proximal end 1010 of push tube 1003. Thereafter, pulling of the handle assembly's trigger 505 will cause ram 515 to move distally along pull rod 1002, whereby push tube 1003 can drive expansion plug 21, 52 into fixation member 20, 50, respectively, so as to fix fixation member 20, 50, and thus graft material 200 in a bone tunnel.

The use of handle assembly 500 in conjunction with pull rod 1002 is often preferred, since it permits pull rod 1002 to be held in place while ram 515 is advanced down pull rod 1002.

More particularly, inasmuch as handle assembly 500 is releasably secured to pull rod 1002 via the engagement of handle gate 555 with pull rod ribs 1008, handle assembly 500 can stabilize pull rod 1002 even as the handle's ram 515 is advancing down pull rod 1002. This has been found to be advantageous in many circumstances. Further details regarding the configuration and use of handle assembly 500 may be found in co-pending application Ser. No. 09/510,770, filed Feb. 23, 2000, which is hereby incorporated by reference.

One of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entirety.

What is claimed is:

1. A ligament graft fixation system for fixing ligament graft material within a bone tunnel comprising:
    an expandable fixation member having opposed bone engaging elements disposed about its periphery, the fixation member having a proximal end, a distal end and an expansion plug receiving opening defined in the proximal end, at least one plug retaining element provided in the expansion plug receiving opening;
    a graft receiving eyelet disposed proximate the distal end of the expandable fixation member;
    an expansion plug having a diameter greater than a diameter of the expansion plug receiving opening and having an engaging element matable with the plug retaining element wherein forceable insertion of the expansion plug into the expansion plug receiving opening causes an expansion of the expandable fixation member driving the opposed bone engaging elements apart so as to fix the bone engaging elements in a bone tunnel;
    a pull rod engaged to the expandable fixation member;
    a push tube abutting the expansion plug; and
    an actuation element engaged to the pull rod and the push tube, the actuation element providing relative movement between the pull rod and the push tube to forceably insert the expansion plug into the expandable fixation member.

2. The ligament graft fixation system of claim 1, wherein at least one expansion slot is formed in a side wall of the expandable fixation member, the expansion slot adapted to direct expansion of the expandable fixation member in a direction so as to drive the opposed bone engaging elements apart.

3. The ligament graft fixation system of claim 2, wherein at least two expansion slots are provided.

4. The ligament graft fixation system of claim 3, wherein the at least two expansion slots are provided asymmetrically about the periphery of the expandable fixation member.

5. The ligament graft fixation system of claim 1, wherein the expandable fixation member includes two graft location grooves, each groove extending distally from one side of the graft receiving eyelet.

6. The ligament graft fixation system of claim 5, wherein the grooves are asymmetrically located to allow for anterior or posterior graft fixation.

7. The ligament graft fixation system of claim 1, wherein the at least one plug retaining element is a female thread formed about the expansion plug receiving opening.

8. The ligament graft fixation system of claim 7, wherein the engaging element is a male thread disposed about a periphery of the expansion plug, the male thread having a pitch approximately equal to a pitch on the female thread formed about the expansion plug receiving opening so that upon forceable insertion of the expansion plug into the expansion plug receiving opening the male and female threads engage to hold the expansion plug within the expansion plug receiving opening.

9. The ligament graft fixation system of claim 1, wherein the expansion plug is cannulated and a pull rod engaging element is disposed on a distal end of the expansion plug receiving opening, the pull rod extending through the cannulated expansion plug and the expansion plug receiving opening and engaging the pull rod engaging element.

10. The ligament graft fixation system of claim 9, wherein the push tube is cannulated and extends over the pull rod and abuts a distal end of the expansion plug.

11. The ligament graft fixation system of claim 1, wherein the graft receiving eyelet is provided on a tip having a proximal expansion plug and the fixation member defines a distal plug receiving opening, the proximal expansion plug sized so that, upon forceable insertion of the proximal expansion plug into the distal plug receiving opening, a distal portion of the expanding fixation member expands for fixing to a bone tunnel.

12. The ligament graft fixation system of claim 11, wherein the expanding fixation element has at least one proximal expansion slot guiding expansion of a proximal portion of the expanding fixation member upon forceable insertion of the expansion plug and at least one distal expansion slot guiding expansion of a proximal portion of the expanding fixation member upon forceable insertion of the proximal expansion plug.

13. The ligament graft fixation system of claim 12, wherein the at least one proximal expansion slot guides expansion of a proximal portion of the expanding fixation member in a first direction and the at least one distal expansion slot guides expansion of a distal portion of the expanding fixation member in a second direction different from the first direction.

14. The ligament graft fixation system of claim 13, wherein the at least one distal expansion slot guides expansion of a distal portion of the expanding fixation member to drive the opposed bone engaging members apart to fix the expanding fixation member in a bone tunnel.

15. The ligament graft fixation system of claim 14, wherein the at least one proximal expansion slot guides expansion of a proximal portion in a direction for pressing a graft material against a bone tunnel wall.

16. The ligament graft fixation system of claim 13, wherein the proximal expansion plug sized so that, upon forceable compression of the expansion plug, expanding fixation member, and proximal plug, the proximal expansion plug is admitted into the distal plug receiving opening before the expansion plug is admitted into the proximal plug receiving opening.

17. The ligament graft fixation system of claim 11, wherein the expansion plug and the expanding fixation member are cannulated and a pull rod engaging element is disposed on a proximal end of the proximal plug, the pull rod extending through the cannulated expansion plug and expanding fixation member and engaging the pull rod engaging element.

18. The ligament graft fixation system of claim 17, wherein the push tube is cannulated and extends over the pull rod and abuts a distal end of the expansion plug.

* * * * *